(12) United States Patent
Avesani et al.

(10) Patent No.: US 12,194,182 B2
(45) Date of Patent: Jan. 14, 2025

(54) PLANT AND METHOD TO CONTINUOUSLY DECONTAMINATE RIGID CONTAINERS

(71) Applicant: COMECER S.p.A., Castel Bolognese (IT)

(72) Inventors: Alessandro Avesani, Castel Bolognese (IT); Martino Nicola Raspadori, Castel Bolognese (IT); Michele Tugnoli, Castel Bolognese (IT); Alessandro Brunetti, Castel Bolognese (IT); Giacomo Guidi, Castel Bolognese (IT)

(73) Assignee: COMECER S.p.A., Castel Bolognese (IT)

( * ) Notice: Subject to any disclaimer, the term of this patent is extended or adjusted under 35 U.S.C. 154(b) by 740 days.

(21) Appl. No.: 17/183,571

(22) Filed: Feb. 24, 2021

(65) Prior Publication Data

US 2021/0260232 A1    Aug. 26, 2021

(30) Foreign Application Priority Data

Feb. 25, 2020  (IT) .......................... 102020000003883

(51) Int. Cl.
*A61L 2/20* (2006.01)
*A61L 2/26* (2006.01)

(52) U.S. Cl.
CPC ................. *A61L 2/208* (2013.01); *A61L 2/26* (2013.01); *A61L 2202/11* (2013.01);
(Continued)

(58) Field of Classification Search
CPC ......... B08B 9/28; B08B 9/30; B05B 13/0609; A47L 15/245; B67C 7/00; A61L 2202/122; A61L 2202/23
See application file for complete search history.

(56) References Cited

U.S. PATENT DOCUMENTS 3,291,143 A * 12/1966 Huddle ..................... B08B 9/30
  248/500
3,952,698 A   4/1976 Beyer et al.
(Continued)

FOREIGN PATENT DOCUMENTS

DE      19945500 A1   4/2000
DE   102017118481 A1   2/2019
(Continued)

OTHER PUBLICATIONS

WO-2019012696-A1_translation (Year: 2019).*
(Continued)

*Primary Examiner* — Kevin Joyner
*Assistant Examiner* — Changru Chen
(74) *Attorney, Agent, or Firm* — Dorsey & Whitney LLP (57) ABSTRACT

A plant to continuously decontaminate containers, comprising: a decontamination chamber having a tray having through openings and a feeding grid to feed at least one row of containers, which are aligned according to a first direction, along the tray, in a second direction, which is transverse to the first direction; a vaporized hydrogen peroxide generator to generate a gaseous mixture comprising air and vaporized hydrogen peroxide; a forced ventilation system to generate, in the chamber, a first flow of gaseous mixture that hits the row of containers from above; and a dispenser system arranged under the tray to generate a second flow of gaseous mixture, which hits the row of containers from below, through the through openings. The feeding grid comprises pushing members uniformly equidistant to each other along the second direction so that any pair of pushing members adjacent to each other can accommodate a row of containers.

9 Claims, 9 Drawing Sheets

(52) U.S. Cl.
   CPC ..... *A61L 2202/122* (2013.01); *A61L 2202/14* (2013.01); *A61L 2202/15* (2013.01); *A61L 2202/23* (2013.01)

(56) References Cited

U.S. PATENT DOCUMENTS

| | | | |
|---|---|---|---|
| 4,092,991 A * | 6/1978 | Rohrs | A47L 15/245 |
| | | | 134/131 |
| 2009/0205746 A1 * | 8/2009 | Yousefpour | B67C 7/00 |
| | | | 53/268 |
| 2013/0028794 A1 | 1/2013 | Silvestri et al. | |
| 2017/0112156 A1 | 4/2017 | Mielnik et al. | |
| 2017/0341791 A1 | 11/2017 | Weiler et al. | |

FOREIGN PATENT DOCUMENTS

| | | | | |
|---|---|---|---|---|
| FR | 3081849 A1 * | 12/2019 | ........... | B65G 47/084 |
| JP | 2004338765 A | 12/2004 | | |
| WO | WO-2016165031 A1 * | 10/2016 | ............... | A61L 2/20 |
| WO | WO-2018158032 A1 * | 9/2018 | ............... | A61L 2/07 |
| WO | WO-2019012696 A1 * | 1/2019 | ............... | A61L 2/20 |

OTHER PUBLICATIONS

FR-3081849-A1_translation (Year: 2019).*
WO-2016165031-A1_translation (Year: 2016).*
WO-2018158032-A1_translation (Year: 2018).*

* cited by examiner

PLANT AND METHOD TO CONTINUOUSLY DECONTAMINATE RIGID CONTAINERS

CROSS-REFERENCE TO RELATED APPLICATIONS

This patent application claims priority from Italian patent application no. 102020000003883 filed on Feb. 25, 2020, the entire disclosure of which is incorporated herein by reference.

TECHNICAL FIELD

This invention relates to a plant and a method to continuously decontaminate containers, in particular rigid containers.

In particular, this invention finds advantageous, but not exclusive, application in reducing the microbiological load on the outer surface of closed rigid containers containing a pharmaceutical substance, such as, for example, bottles, tubs, and nests, by using vaporized hydrogen peroxide (VHP), also known as vapour phase hydrogen peroxide (VPHP), to which the following description refers without any loss of generality thereby.

STATE OF THE PRIOR ART

The most common way to decontaminate the outer surface of rigid containers, such as bottles, containing pharmaceutical substances is to immerse the bottles in an atmosphere saturated with VHP for the period of time necessary to reduce the microbiological load that may be present on the outer surface of the bottles.

Decontamination takes place by performing a cycle inside an isolated chamber wherein the bottles are placed. This cycle typically comprises the following sequence of steps:
- dehumidification, wherein the atmosphere in the chamber is brought to a sufficiently low initial relative humidity;
- conditioning, wherein VHP is introduced into the chamber by means of a device containing a VHP generator until the VHP reaches a predetermined concentration value, for example between 700 and 1200 ppm; the increase in VHP concentration corresponds to an increase in relative humidity, up to a value between 80% and 90%;
- decontamination, wherein the VHP concentration and relative humidity are kept constant at predetermined values for the period of time necessary to reduce the bacteriological load below a predetermined level; and
- aeration, in which VHP is sucked from the chamber using the above-mentioned equipment until the VHP concentration falls below values that are not dangerous to operators.

It is clear that the above-mentioned decontamination cycle is not suitable for being integrated into a bottle filling and/or packaging line, as it involves a significant wait time for the work stations that are upstream and the chamber wherein the downstream of isolated decontamination takes place. The wait time is the sum of the times of the individual steps described above, which in turn depend on the volume of the isolated chamber and the quantity of bottles placed in the isolated chamber. To reduce the wait time, I would have to have a very small isolated chamber and insert a few bottles at a time, but then the performance of the filling and/or packaging line would be very poor.

SUBJECT OF THE INVENTION

The purpose of this invention is to provide a plant and a method to decontaminate the outer surface of pharmaceutical bottles, which does not have the drawbacks described above and, at the same time, is simple and economical to produce.

In accordance with this invention, a plant and a method to continuously decontaminate containers, according to what is set forth in the attached claims, are provided.

BRIEF DESCRIPTION OF THE DRAWINGS

This invention will now be described with reference to the accompanying drawings, which illustrate a non-limiting embodiment thereof, wherein.

PREFERRED EMBODIMENT OF THE INVENTION

Figure 1:
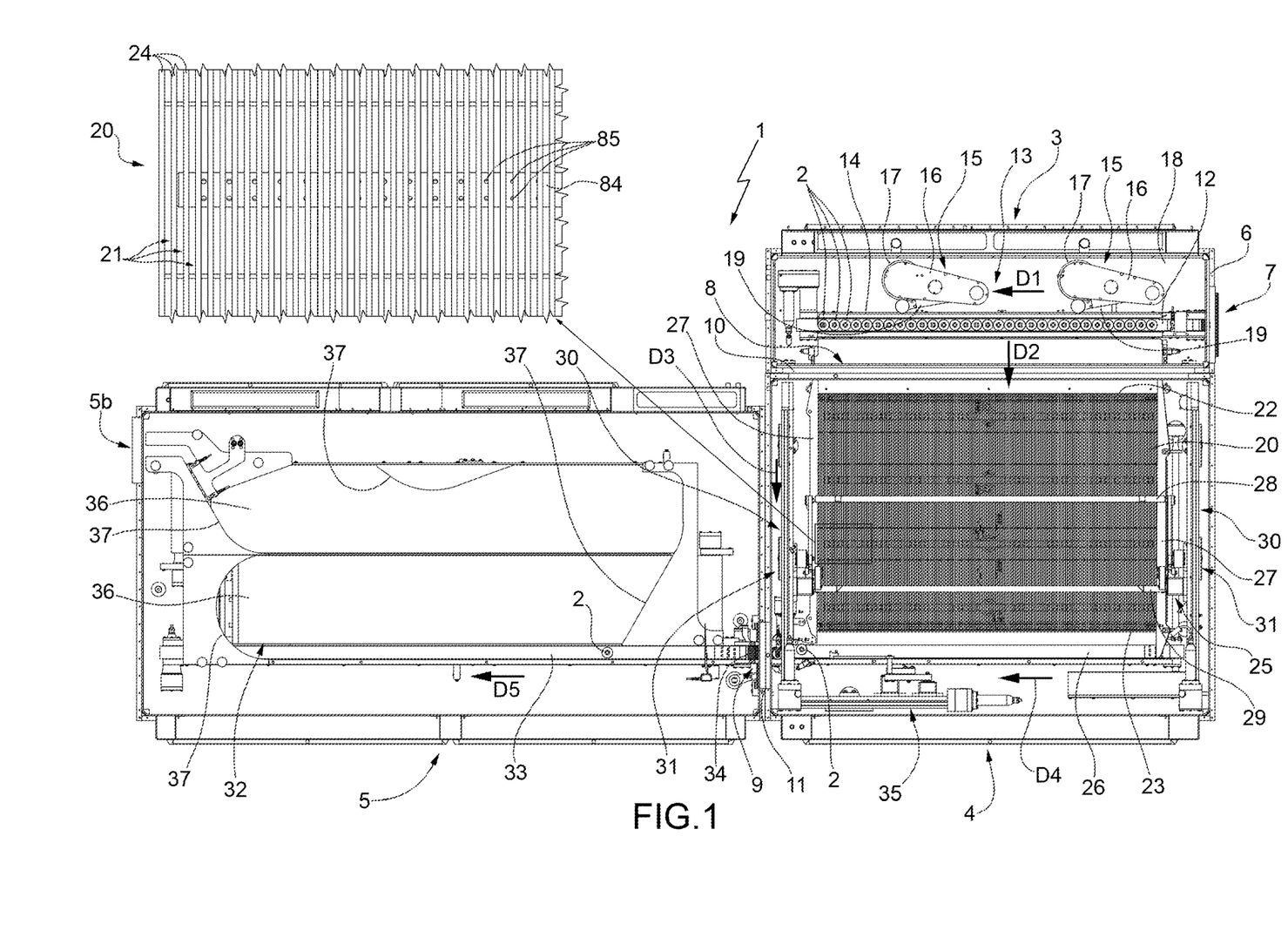
FIGS. 1 and 2 illustrate, according to the same plan view, the interior of the plant of this invention during two respective operating steps of the plant.
Figure 2:
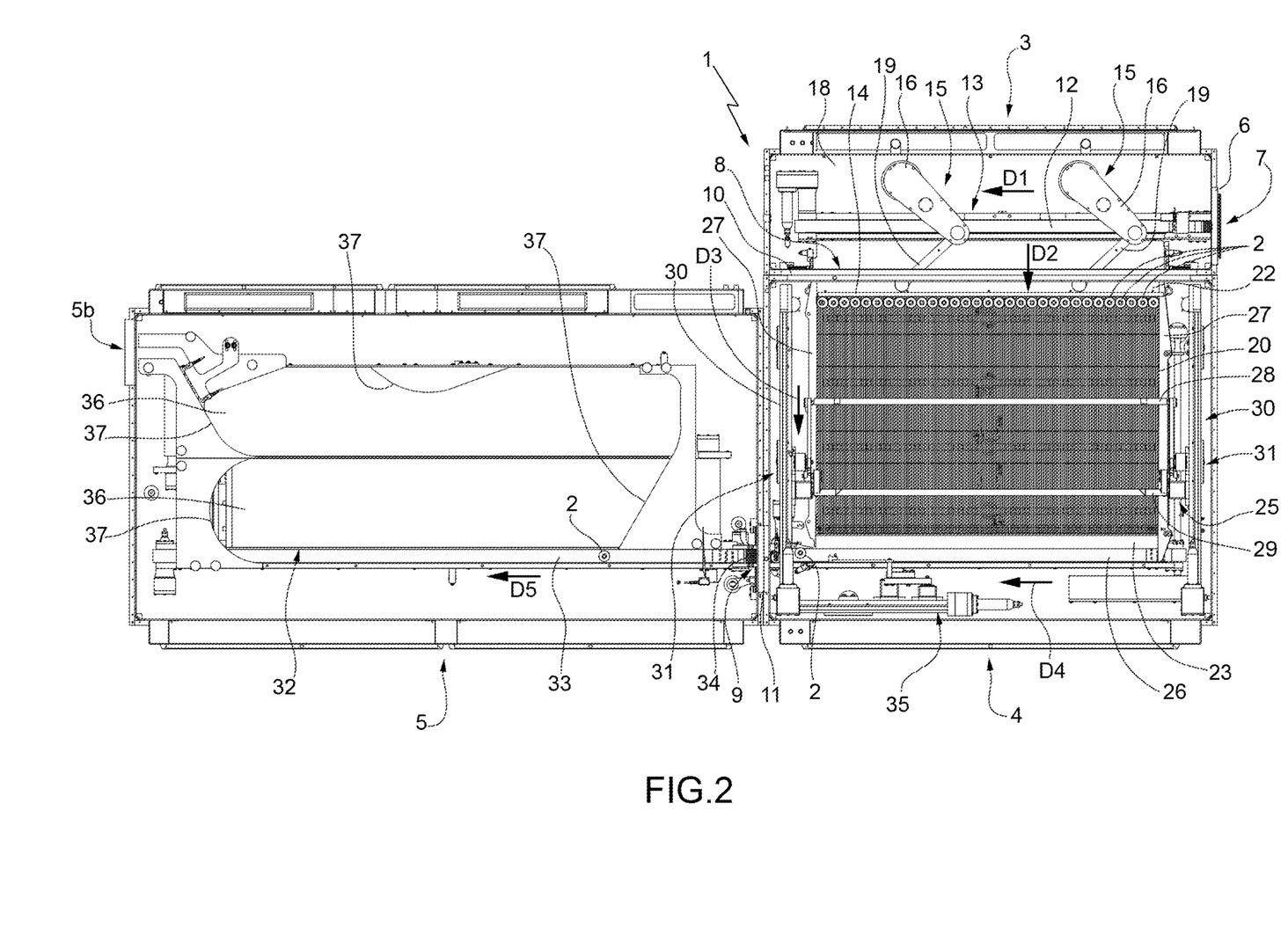

In FIGS. 1 and 2, the number 1 indicates, as a whole, the plant of this invention to continuously decontaminate rigid containers, and in particular drug bottles, indicated by 2.

The plant 1 comprises a compensation chamber 3, a decontamination chamber 4, and an aeration chamber 5. In particular, a wall 6 of the compensation chamber 3 has an inlet opening 7, which is designed to receive the containers 2 from an external conveyor (not illustrated). The decontamination chamber 4 communicates with the compensation chamber 3 through a first connection opening 8 and with the aeration chamber 5 through a second connection opening 9. The connection opening 8 is formed in a wall 10 separating the decontamination chamber 4 from the compensation chamber 3, and the connection opening 9 is formed in a wall 11 separating the decontamination chamber 4 from the aeration chamber 5. In the example illustrated in the figures, each of the walls 10 and 11 is a double wall formed by bringing together two individual walls of the relative two adjoining chambers.

The compensation chamber 3 comprises a belt conveyor 12 for receiving containers 2, one at a time, from the inlet opening 7 and conveying them in a horizontal feeding direction D1 so as to form one row of containers 2 that is arranged in front of the connection opening 8.

The compensation chamber 3 comprises a transfer system 13 for transferring the whole row of containers 2 from the compensation chamber 3 (FIG. 1) to the decontamination chamber 4 (FIG. 2) through the connection opening 8 in a transfer direction D2 that is horizontal and transverse to the direction D1. In particular, the direction D2 is orthogonal to the other direction D1. To this end, the connection opening 8 has a length at least equal to the row of containers 2 that is formed by the belt conveyor 12.

More specifically, the transfer system 13 comprises a pushing member 14 consisting of an oblong element designed to push the whole row of containers 2 in the direction D2 and two connecting rod-crank devices 15, each of which has a crank 16 mounted rotating on a respective base 17 integral with a base wall 18 of the compensation chamber 3 to rotate about a respective axis 16a (FIGS. 3 and 4) perpendicular to a lying plane of the directions D1 and D2, i.e. a vertical axis, and a connecting rod 19 connecting the crank 16 to the pushing member 14.

The connecting rod-crank devices 15 are motorised by means of actuators (not illustrated) housed in the bases 17 to rotate the cranks 16 according to an angular displacement that causes the pushing member 14 to translate in the direction D2 between a rest position (FIG. 1), in which the pushing member 14 is located along one side of the belt conveyor 12 to wait for the formation of the row of containers 2, and a feeding position (FIG. 2), in which the pushing member 14 is located beyond the opposite side of the belt conveyor 12, in particular beyond the connection opening 8, and, thus, feeds the row of containers 2 to the decontamination chamber 4.

The decontamination chamber 4 comprises a tray 20 that has a plurality of slots 21, which can be seen more clearly in the enlarged detail in FIG. 1. The tray 20 comprises an input side 22 and an output side for the row of containers 2. The slots basically extend from the input side 22 to the output side 23 of the tray 20. In particular, the tray 20 is a grid comprising a plurality of equidistant slats 24 to form the slots 21. The input side 22 is arranged along the connection opening 8. In the feeding position, the pushing member 14 positions the row of containers 2 along the input side 22 (FIG. 2).

The decontamination chamber 4 comprises a feeding system 25 for feeding rows of containers 2 on the tray 20 from the input side 22 to the output side 23, according to a feeding direction D3 that is horizontal and transverse to the direction D1. In particular, the direction D3 is orthogonal to a second direction D1 and, therefore, parallel to a third direction D2. The slots 21 of the tray 20 are parallel to the direction D3.

The decontamination chamber 4 also comprises a belt conveyor 26 arranged along the output side 23 of the tray 20 so as to receive a whole row of containers 2 and convey the containers 2 towards the connection opening 9 according to a feeding direction D4 transverse to the direction D3. In particular, the direction D4 is orthogonal to a second direction D3. The feeding system 25 also takes care of transferring an entire of row of containers 2 from the output side 23 of the tray 20 to the belt conveyor 26.

The decontamination chamber 4 also comprises two edges 27 arranged at the sides of the tray 20 and parallel to the direction D3 to prevent the containers 2 from exiting the tray 20 while they are fed onto the tray 20.

The feeding system 25 comprises two pushing members 28 and 29, each of which comprises an oblong element arranged above the tray 20 transversely, and in particular, orthogonally, to the direction D3, two guiding assemblies 30 arranged on opposite sides of the tray 20, with respect to a centreline of the tray 20 parallel to the direction D3, and two raising devices 31, which support the two pushing members 28 and 29 on longitudinal ends thereof and each of which is movably mounted along a corresponding guiding assembly 30 to move the pushing members 28 and 29 parallel to the direction D3. The pushing member 29 is located in front of the second pushing member 28 in the direction D3. As will be more fully described below herein, the raising devices 31 are designed to lower or raise a first pushing member 28 and rigidly do the opposite with the other pushing member 29, i.e. raising or lowering the pushing member 29, for the purpose of using the pushing member 28 to feed a row of containers 2 along the tray 20 in the direction D3, or using the pushing member 29 to transfer a row of containers 2 from the tray 20 to the belt conveyor 26.

The aeration chamber 5 comprises a motorised storage table 32 and a belt conveyor 33 to receive a row of containers 2 from the connection opening 9 and feed the containers 2 to the storage table 32 according to a feeding direction D5. The direction D5 is preferably parallel to a second direction D4. An idle-roller plane 34 is arranged astride the connection opening 9 to ensure the path's continuity during the movement of the containers 2 between the belt conveyors 26 and 33.

The decontamination chamber 4 comprises a transfer system 35 arranged alongside the belt conveyor 26 for pushing the containers 2 remaining on the idle-roller plane 34 out of the connection opening 9, in the direction D4.

The storage table 32 comprises two contiguous, motorised round-trip belts 36 and a plurality of accompanying guides 37 arranged over part of the belts 36 and suitably shaped to define a container storage path 2. This storage path terminates at an output opening 5b of the aeration chamber 5.

The plant 1 comprises a plurality of presence sensors (not illustrated) for detecting the presence of the containers 2 at various points along their path inside the plant 1, for example: in the compensation chamber 3 at the end of the belt conveyor 12, in the decontamination chamber 4 on the input side 22 and on the output side 23 of the tray 20 and on the belt conveyor 26, and in the aeration chamber 5 at the connection opening 9. It also comprises an electronic control unit (not illustrated) configured to control and synchronise the actuators of the belt conveyors 12, 26, and 33, of the feeding system 25, of the transfer systems 13, and 35 and of the storage table 32, according to the signals received from the presence sensors.

Figure 3:
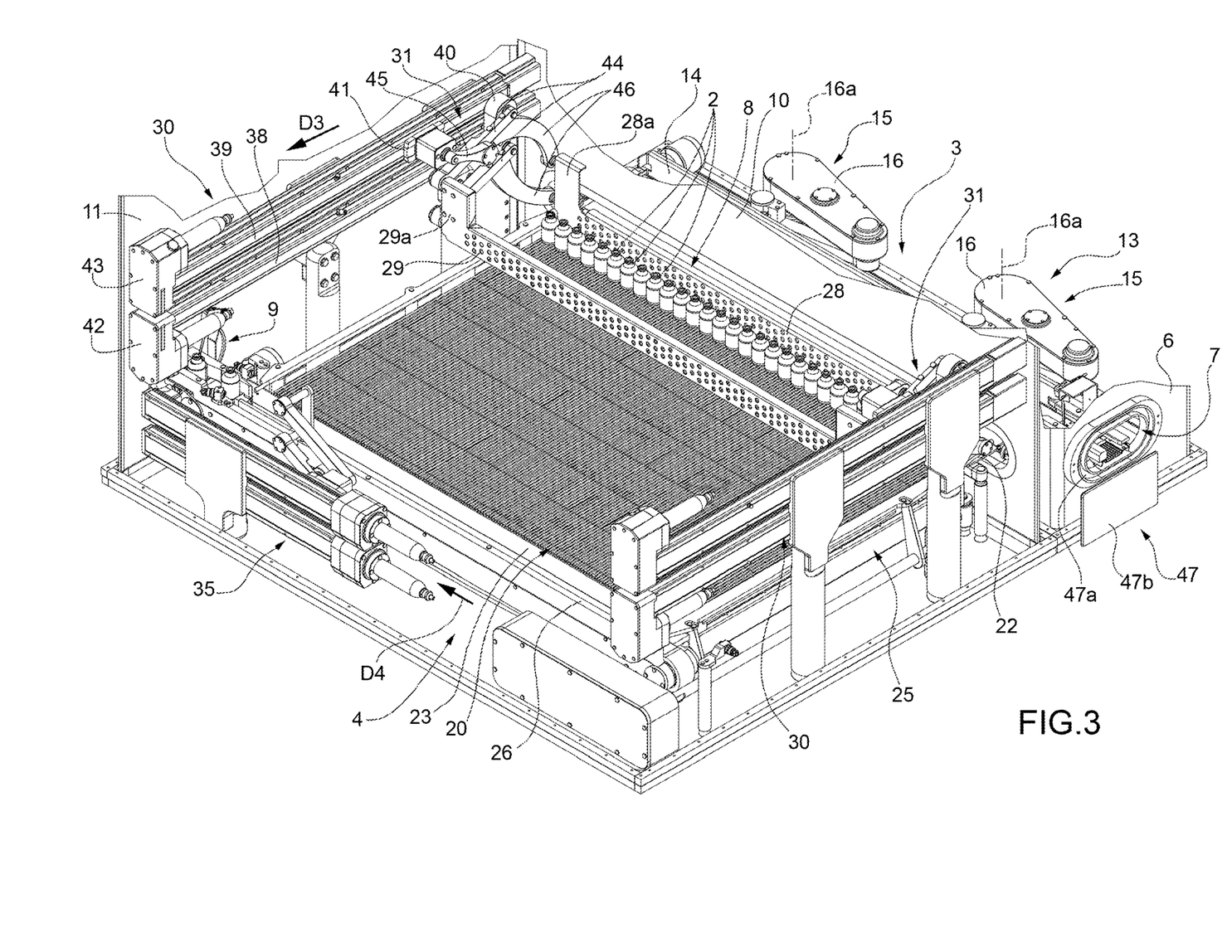
FIGS. 3 and 4 illustrate, according to an axonometric view with some parts removed and other parts cut off, a decontamination chamber of the plant in FIGS. 1 and 2 during two additional, respective operating steps of the plant.
Figure 4:
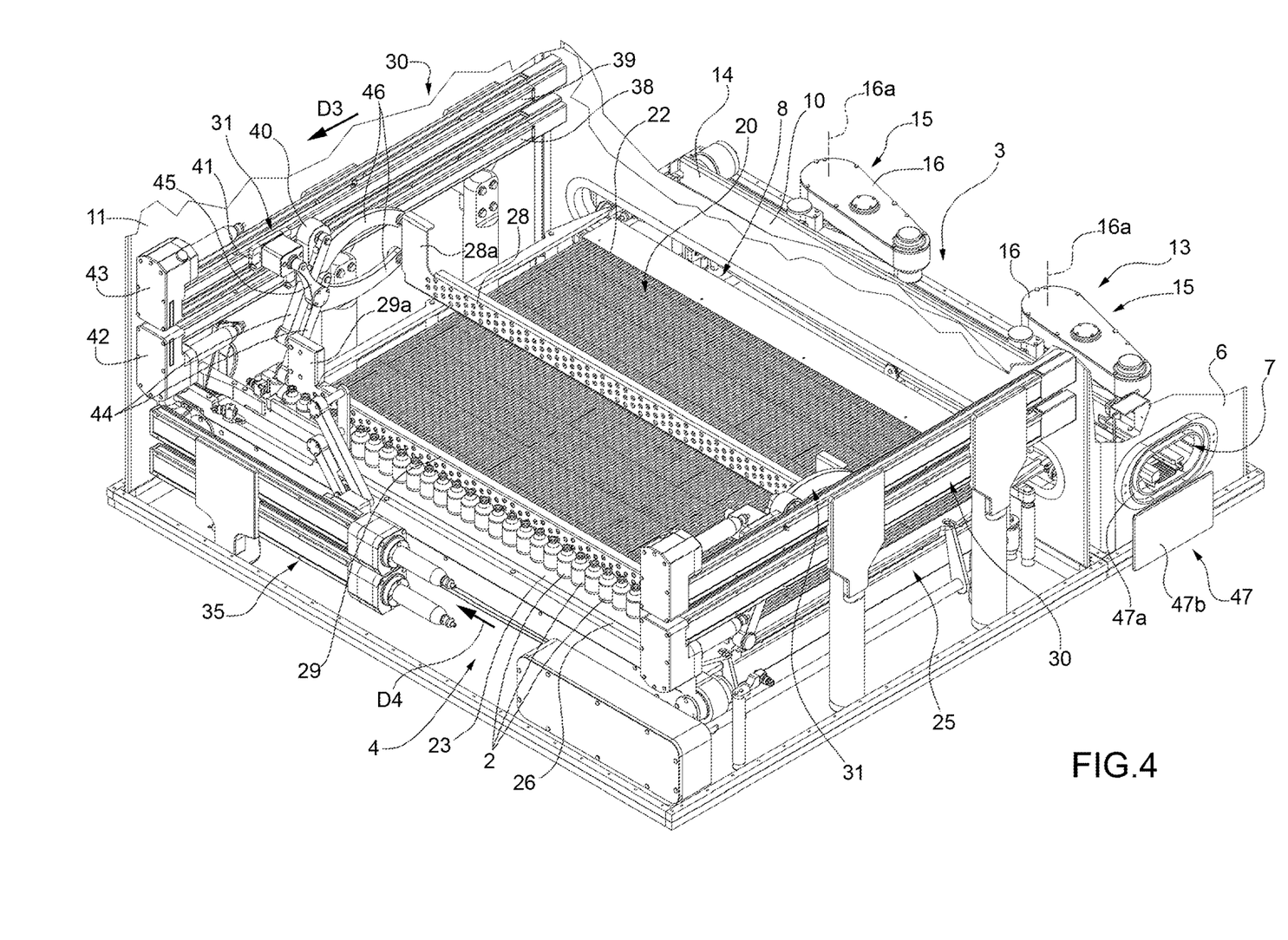

With reference to FIGS. 3 and 4, each guiding assembly 30 comprises two guides 38 and 39 that are horizontal and parallel to the direction D3 and mounted above each other. Each raising device 31 comprises two slides 40 and 41, each of which is slidably coupled to a corresponding guide 38, 39 via a respective recirculating ball screw (not illustrated) driven by a respective electric actuator 42, 43. The slide 41 is further forward than the second slide 40 in the direction D3.

The raising device 31 comprises two arms 44, which connect the slide 40 to a longitudinal end portion 29a of the pushing member 29 to form an articulated parallelogram, and a third arm 45, which has a first longitudinal end articulated to the other slide 41 to rotate about a horizontal axis and a second longitudinal end articulated to an intermediate point of one of the arms 44 to rotate about another horizontal axis.

The raising device 31 comprises two additional arms 46, each of which has a first longitudinal end attached to a respective arm 44 at one end of the arm 44 connected to the slide 40 and a second longitudinal end articulated to a longitudinal end portion 28a of the pushing member 28 to rotate about a horizontal axis. The two arms 46 are curved. In other words, the two arms 46 constitute a kind of extension of the arms 44 that connect the slide 40 to the longitudinal end portion 28a of the pushing member 28 so as to form another articulated parallelogram.

FIG. 3 shows the feeding system 25 in a feeding configuration, wherein the slides 40 and 41 are at the maximum distance from each other, and thus the pushing member 28 is lowered to the height of the containers 2 and the other pushing member 29 is raised above the containers 2. The slides are arranged near the connection opening 7 so that the pushing member 28 is arranged behind a row of containers 2, in the direction D3, that is located on the input side 22 of the tray 20, ready to push the row of containers 2 along the tray 20 in the direction D3.

FIG. 4 shows the feeding system 25 in an unloading configuration, wherein the slides 40 and 41 are at the minimum distance from each other, and thus the pushing member 28 is raised above the containers 2 and the other pushing member 29 is lowered to the height of the containers 2. The slides are arranged close to the belt conveyor 26 so that the pushing member 29 is arranged behind a row of containers 2, in the direction D3, that is located on the output side 23 of the tray 20, ready to push the row of containers 2 onto the belt conveyor 26.

Again with reference to FIGS. 3 and 4, wherein part of the compensation chamber 3 and of the relative transfer system 13 is also visible, the inlet opening 7 is provided with a respective hermetically sealing shutter, indicated with 47. The shutter 47 comprises a corresponding annular seal (not illustrated), which is arranged in a groove 47a formed in the wall 6 and surrounding the inlet opening 7, and a respective movable panel 47b. The panel 47b is moved by a corresponding actuator (not illustrated) to vertically translate to and from a closed position, wherein the panel 47b itself closes the inlet opening 7 by squeezing the respective annular seal.

Figure 5:
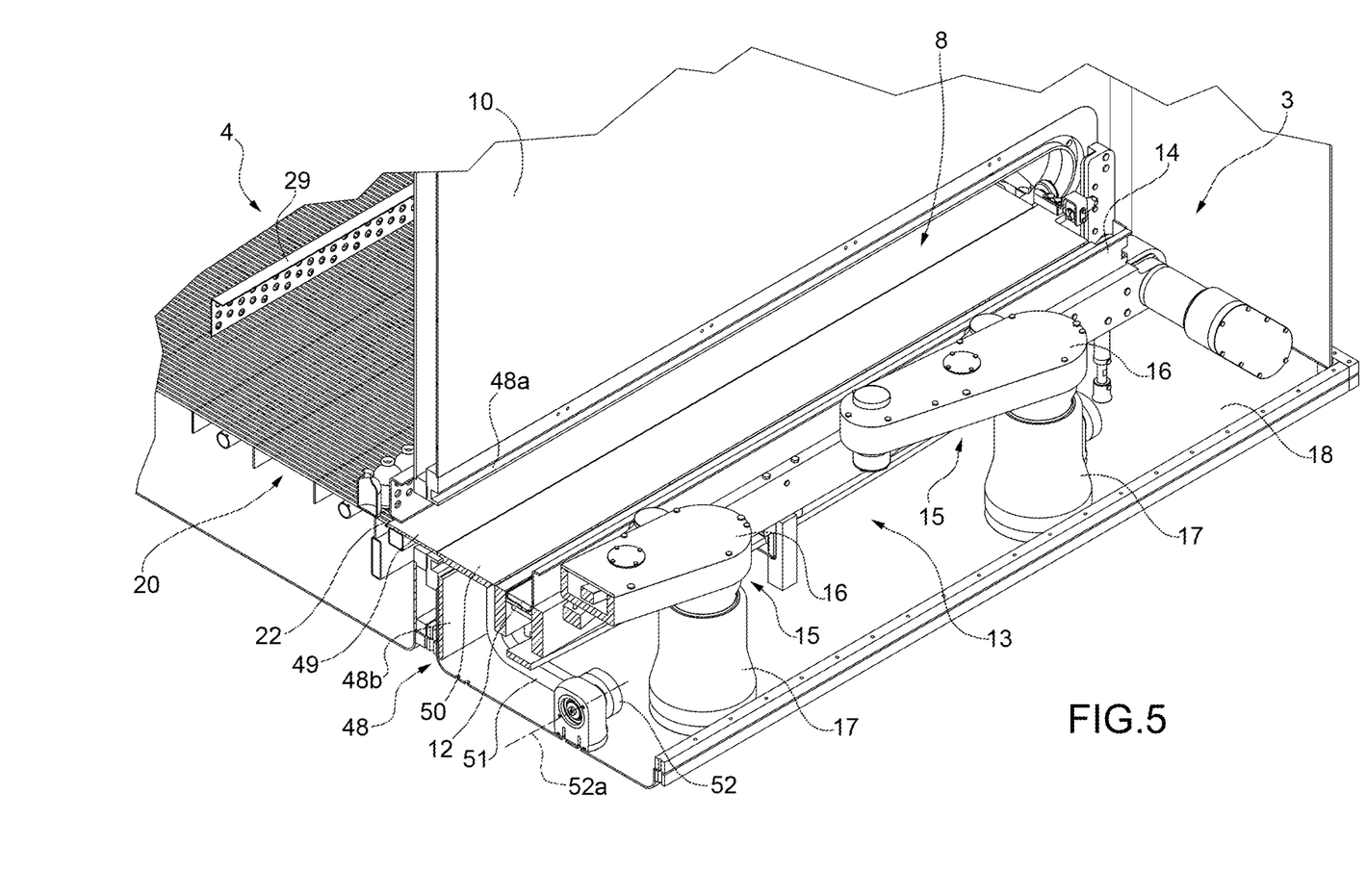
FIG. 5 illustrates, in greater detail, according to an axonometric view and in cross-section along a vertical plane, a part of a compensation chamber of the plant in FIGS. 1 and 2.

With reference to FIG. 5, the connection opening 8 is provided with a hermetically sealing shutter, indicated by 48. The shutter 48 comprises a corresponding annular seal (not illustrated), which is arranged in a groove 48a formed in the wall 10 and surrounding the connection opening 8, and a respective movable panel 48b. The panel 48b is moved by a corresponding actuator (not illustrated) to vertically translate to and from a closed position, wherein the panel 48b itself closes the connection opening 8 by squeezing the respective annular seal.

Again with reference to FIG. 5, a fixed flat element 49 and a movable flat element 50 are placed between the belt conveyor 12 and the tray 20 to ensure the path's continuity in transferring the containers 2 from the compensation chamber 3 to the decontamination chamber 4.

The fixed flat element 49 passes through the connection opening 8 to the input side 22 of the tray 20. The movable flat element 50 is placed between the flat element 49 and the belt conveyor 12 and is supported by two L-shaped arms 51 (only one of which is visible in FIG. 5), which have respective ends 52 hinged to the base wall 18 of the compensation chamber 3 to rotate around a horizontal axis 52a so as to allow the flat element 50 to rotate between an operating position, which is the one illustrated in FIG. 5, wherein the flat element 50 is coplanar to the second flat element 49 and to the transport plane of the belt conveyor 12, and a raised position, wherein a passage for the panel 48b of the shutter 48 opens between the flat elements 49 and 50. In fact, the panel 48b is movable between an open position, wherein it is located below the flat element 50 and therefore leaves the connection opening 8 free, and a closed position, in which the panel 48b raises the flat element 50 and closes the connection opening 8.

Figures 6, 7:
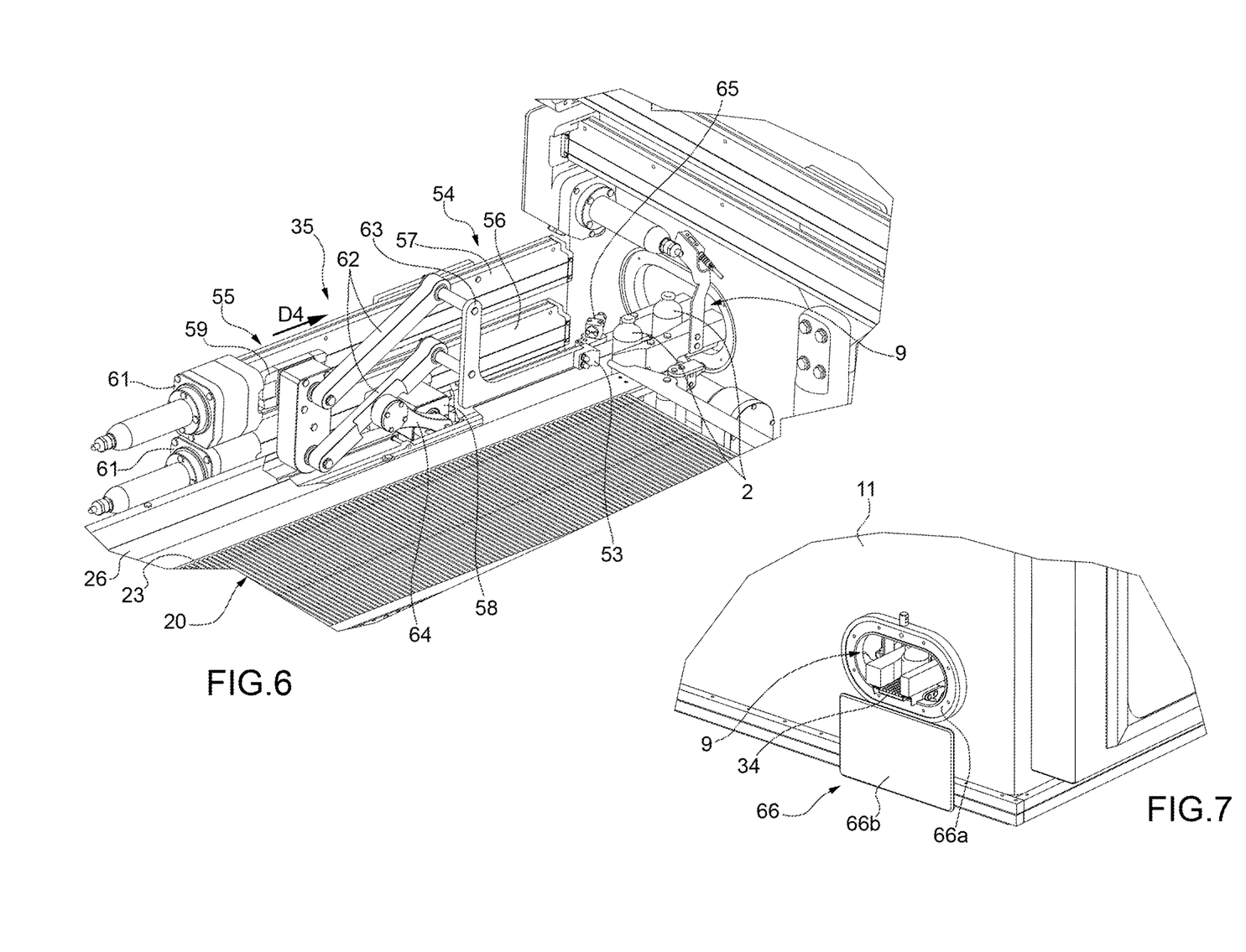
FIGS. 6 and 7 illustrate in greater detail, according to two respective, partially cut-off axonometric views, two parts of the decontamination chamber in FIGS. 3 and 4.

With reference to FIG. 6, the transfer system 35 comprises a pushing member 53 arranged above the belt conveyor 26, a guiding assembly 54 having a structure similar to the other guiding assembly 30 (FIGS. 3 and 4), and a raising device 55, which supports the pushing member 53, is movably mounted along the guiding assembly 54 to move the pushing member 53 parallel to the direction D4, and has a structure similar to the other raising device 31 (FIGS. 3 and 4) to lower the pushing member 53 towards the belt conveyor 26 in order to push the containers 2 (this situation is illustrated in FIG. 6), and to raise the pushing member 53 above the containers 2 in order to allow the belt conveyor 26 to receive a row of containers 2.

In particular, the guiding assembly 54 comprises two guides 56 and 57 that are horizontal and parallel to the direction D4 and mounted above each other. The raising device 55 comprises two slides 58 and 59, each of which is slidably coupled to a corresponding guide 56, 57 via a respective recirculating ball screw (not illustrated) driven by a respective electric actuator 60, 61. The slide 58 is further forward than the slide 59 in the direction D4.

The raising device 55 comprises two arms 62, which connect the slide 59 to an end support 63 of the pushing member 53 to form an articulated parallelogram, and a third arm 64, which has a first longitudinal end articulated to the other slide 58 to rotate about a horizontal axis and a second longitudinal end articulated to an intermediate point of one of the arms 62 to rotate about another horizontal axis. When the slides 58 and 59 are at the maximum distance from each other, the pushing member 53 is lowered to the height of the containers 2. When, on the other hand, the slides 58 and 59 are at the minimum distance from each other, the pushing member 53 is raised above the containers 2.

FIG. 6 shows a presence sensor 65 arranged at one end of the belt conveyor 26 near the connection opening 9 for detecting when a row of containers 2 is loaded onto the belt conveyor 26 and when the latter has transferred the entire row of containers 2 onto the idle-roller plane 14 for the purpose of activating/deactivating the belt conveyor 26 and synchronising the movement of the transfer system 35 with activation/deactivation of the belt conveyor 26.

With reference to FIG. 7, the connection opening 9 is provided with a corresponding hermetically sealing shutter, indicated by 66. The shutter 66 comprises a corresponding annular seal (not illustrated), which is arranged in a groove 66a formed in the wall 11 and surrounding the connection opening 9, and a respective movable panel 66b. The panel 66b is moved by a corresponding actuator (not illustrated) to vertically translate to and from a closed position, wherein the panel 66b itself closes the connection opening 9 by squeezing the corresponding annular seal. 7 Figure illustrates a portion of the idle-roller plane 34 which passes through the connection opening 9 and which is divided into two portions to allow its ascent from the panel 66b.

The opening and closing of the shutter 66 is coordinated with the activation of the belt conveyor 26 and the movement of the transfer system 35.

Figure 8:
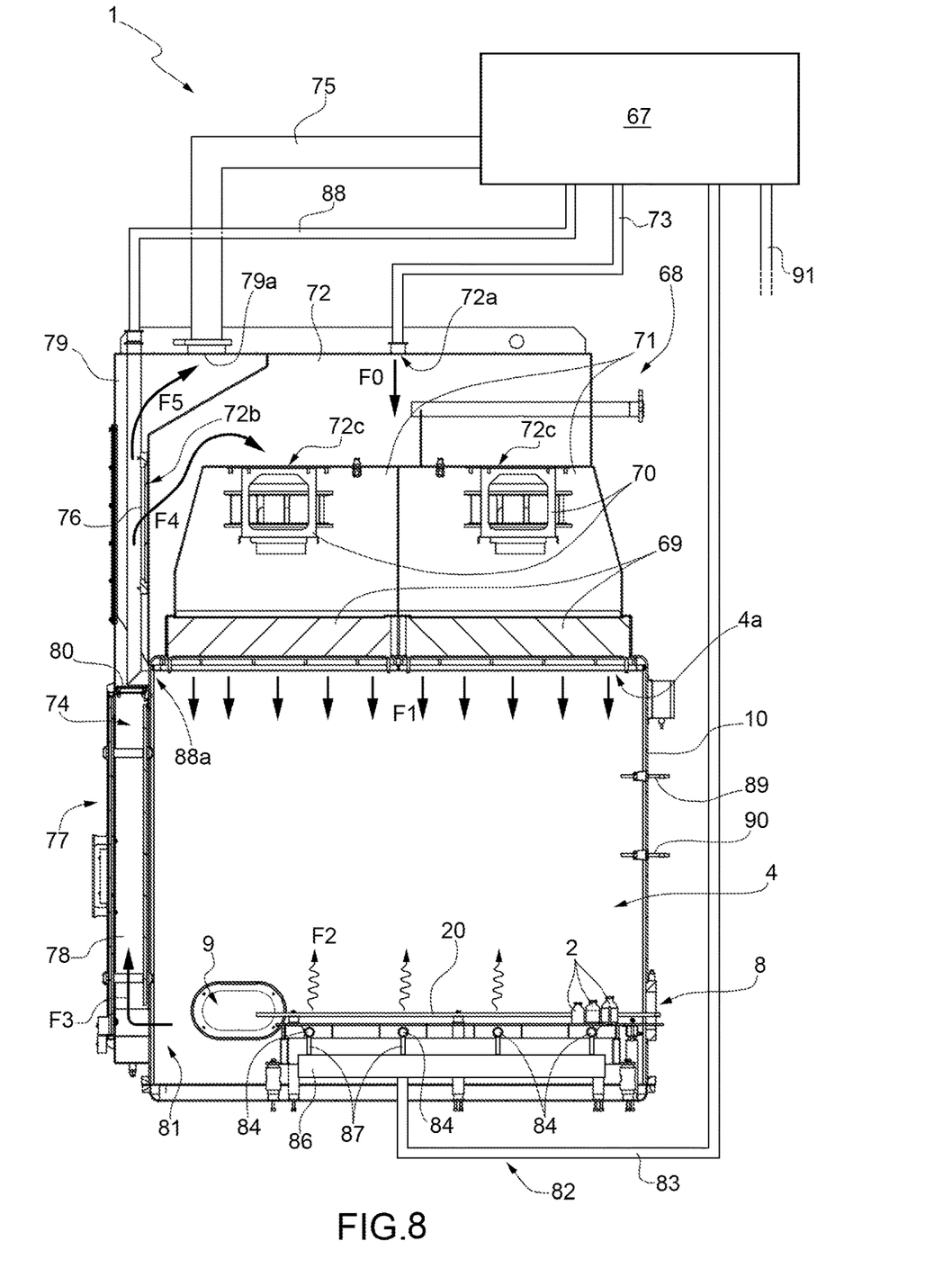
FIG. 8 illustrates the decontamination chamber of the plant in FIGS. 1 and 2 according to a vertical cross-section view.

With reference to FIG. 8, in which the feeding system 25, the belt conveyor 26, and the transfer system 35 are not illustrated, for the sake of clarity, the plant 1 comprises a VHP generator 67 for generating a gaseous mixture comprising air and VHP, and a forced ventilation system 68, which is connected to the VHP generator 67 to receive the gaseous mixture and to the decontamination chamber 4 in such a way as to generate a flow of gaseous mixture F1 in the chamber oriented so as to hit the containers 2 present in the decontamination chamber 4 from above. Advantageously, the forced ventilation system 68 comprises a plurality of filters 69 arranged so as to define a ceiling 4a of the decontamination chamber 4 and comprises at least one fan compressor 70 for pushing the gaseous mixture through the filters 69 so that the flow of gaseous mixture F1 is a laminar flow directed top-down.

In particular, the forced ventilation system 68 comprises one or more chambers 71 (FIG. 8 shows two chambers 71), each of which houses a corresponding fan compressor 70 and communicates with the decontamination chamber 4 through a corresponding filter assembly 69, and an additional chamber 72, which partially surrounds the chambers 71 and comprises a feeding inlet 72a connected with the VHP generator 67 through a delivery duct 73 and one or more outlets 72c, each of which is connected to, and in particular coincides with, the inlet of a corresponding fan compressor 70.

The decontamination chamber 4 comprises a recirculation circuit 74, which connects the internal volume of the decontamination chamber 4, at an area basically at the level of the tray 20, to the chamber 72 through an intake inlet 72b of the chamber 72 and to the VHP generator 67 through a return duct 75. The intake inlet 72b is provided with a grid 76 having an adjustable cross section to adjust the ratio between the flow of gas mixture entering the chamber 72 and the flow of gas mixture returning to the VHP generator 67.

The recirculation circuit 74 is defined by one or more interconnecting cavities of an outer casing of the decontamination chamber 4, said outer casing comprising a hatch 77. In particular, the recirculation circuit 74 comprises a first cavity 78, which is defined inside the hatch 77, and a second cavity 79, which is arranged above the hatch 77, wraps around at least part of the chamber 72 and communicates with the cavity 78 through an upper grid 80 of the hatch 77. The cavity 78 communicates with the internal volume of the decontamination chamber 4 through a lower slot 81 formed on the internal face of the hatch 77 along a horizontal side of the hatch 77, at the level of the tray 20. The cavity 79 communicates with the chamber 72 through the intake inlet 72b and comprises an outlet 79b connected with the return duct 75.

With reference to FIGS. 8 and 1, the plant 1 comprises a dispenser system 82, which is arranged in the decontamination chamber 4 and is connected to the VHP generator 67 via a delivery duct 83 to receive the gaseous mixture and comprises a plurality of dispenser bodies 84 arranged below the tray 20 to generate a flow of gaseous mixture F2 (FIG. 8) in the decontamination chamber 4, the flow being oriented so as to hit the containers 2 present in the decontamination chamber 4 from below through the slots 21 of the tray 20.

Advantageously, the dispenser bodies 84 consist of respective tubular bodies, each of which has a plurality of through holes 85 (FIG. 1) oriented towards the tray 20 and having a cross-section area smaller than the cross-section area of the dispenser bodies 84 so that the flow of gaseous mixture F2 is a turbulent flow hitting the containers 2 from below. The dispenser bodies 84 are parallel and equidistant from each other in the direction D3, and the holes 85 are evenly distributed along each dispenser body 84 so that the flow of gaseous mixture F2 is evenly distributed in the area of the tray 20.

In particular, the dispenser system 82 comprises at least one manifold 86, which receives the gaseous mixture from the delivery duct 83 and distributes it to the dispenser bodies 84 through as many ducts 87.

The system 1 comprises an additional delivery duct 88 connecting the VHP generator 67 directly with the interior volume of the decontamination chamber 4 at a portion of a vertical interior wall of the decontamination chamber 4 close to the ceiling 4a. In particular, the delivery duct 88 passes through the cavity 79 and terminates with its own outlet 88a in a portion of a vertical inner wall of the decontamination chamber 4 located above the hatch 77. The delivery duct 88 is used to perform initial decontamination cycles for the entire plant 1, and in particular for the decontamination chamber 4, in the absence of the containers 2.

The system 1 comprises a VHP sensor 89, which is arranged in the decontamination chamber 4 to measure the VHP concentration. The electronic control unit is configured to control the VHP generator 67 and the forced ventilation system 68, and thus ultimately the generation of the two flows of gas mixture F1 and F2, depending on the signal provided by the VHP sensor 89 to maintain the VHP concentration of the gas mixture in the decontamination chamber 4 at a predetermined VHPSET value ranging between 700 and 1200 ppm. The VHP generator 67, which is of a basically known type, is controlled in terms of the amount of vaporized hydrogen peroxide per unit of time. The ventilation system 68 is controlled in terms of adjusting the speed of the fan compressors 70 and the grid 76 passage section.

The VHPSET concentration value is preselected depending on the type of container 2 and on the average speed at which it moves through the decontamination chamber 4.

The plant 1 also comprises a humidity sensor 90, which is arranged in the decontamination chamber 4 to measure the relative humidity. The electronic control unit is configured to control the VHP generator 67 and the forced ventilation system 68 according to the signal provided by the humidity sensor 90 to maintain the relative humidity in the decontamination chamber 4 at a predetermined HRSET value ranging between 80% and 90%.

According to different embodiments, the electronic control unit is configured to control the VHP generator 67 and the forced ventilation system 68 in an open ring, i.e. without using the VHP sensor 89, in order to keep the VHP concentration at the desired VHPSET value, and/or without using the VHP sensor 90, in order to keep the relative humidity at the desired HRSET value.

It should be noted that maintaining the relative humidity HRSET value is correlated with maintaining the VHP concentration VHPSET value.

The plant 1 comprises an additional delivery duct 91 connecting the VHP generator 67 directly with the inner volume of the compensation chamber 3. The electronic control unit is configured to control the VHP generator 67 so that it feeds the gaseous mixture of air and VHP to the delivery duct 91 independently of the other delivery ducts 73, 83, and 88.

Again with reference to FIG. 8, in use, the gaseous mixture comprising air and VHP generated by the VHP generator 67 is fed to the chamber 72 through the delivery duct 73 (flow indicated by F0 in FIG. 8). The gaseous mixture passes from the chamber 72 to the other chambers 71 due to the fan compressor 70 suction action. Inside each chamber 71, the corresponding fan compressor 70 pushes the gaseous mixture towards the corresponding filters 69 so as to generate, in the decontamination chamber 4, the flow of gaseous mixture F1 that hits the containers 2 from above. The flow of gaseous mixture F1 touches the upper and side outer surfaces of the containers 2 to a greater extent so that the VHP of the gaseous mixture can reduce the microbiological load present on these surfaces.

The gaseous mixture is also fed to the dispenser system 82 through the delivery duct 83, and the dispenser system 82 generates in the decontamination chamber 4 the flow of gaseous mixture F2 that hits the containers 2 from below through the slots 21 of the tray 20. The flow of gaseous mixture F2 touches the lower outer surfaces of the containers 2 to a greater extent so that the VHP of the gaseous mixture can reduce the microbiological load present on these surfaces.

The two flows of gaseous mixture F1 and F2 basically mix in the tray 20. The gaseous mixture exits the decontamination chamber 4 through the lower slot 81 of the hatch 77 to enter the recirculation circuit 74, collected in a flow indicated by F3 in FIG. 8. The flow of gaseous mixture F3 moves through the cavity 78 and reaches the other cavity 79 where it splits into two flows of gaseous mixture F4 and F5. The flow F4 enters the chamber 72 through the intake inlet 72*b* and the other flow F5 exits the cavity 79 through the outlet 79*a* before returning to the VHP generator 67 via the return duct 75.

In the chamber 72, the flow of gaseous mixture F4 mixes with the other flow of gaseous mixture F0 fed by the VHP generator 67. The mixed gaseous mixture is sucked by the fan compressors 70 back to the decontamination chamber 4. The VHP generator 67 regenerates, in a known way, the gaseous mixture arriving from the return duct 75 by enriching it with a suitable amount of VHP.

Figure 9:
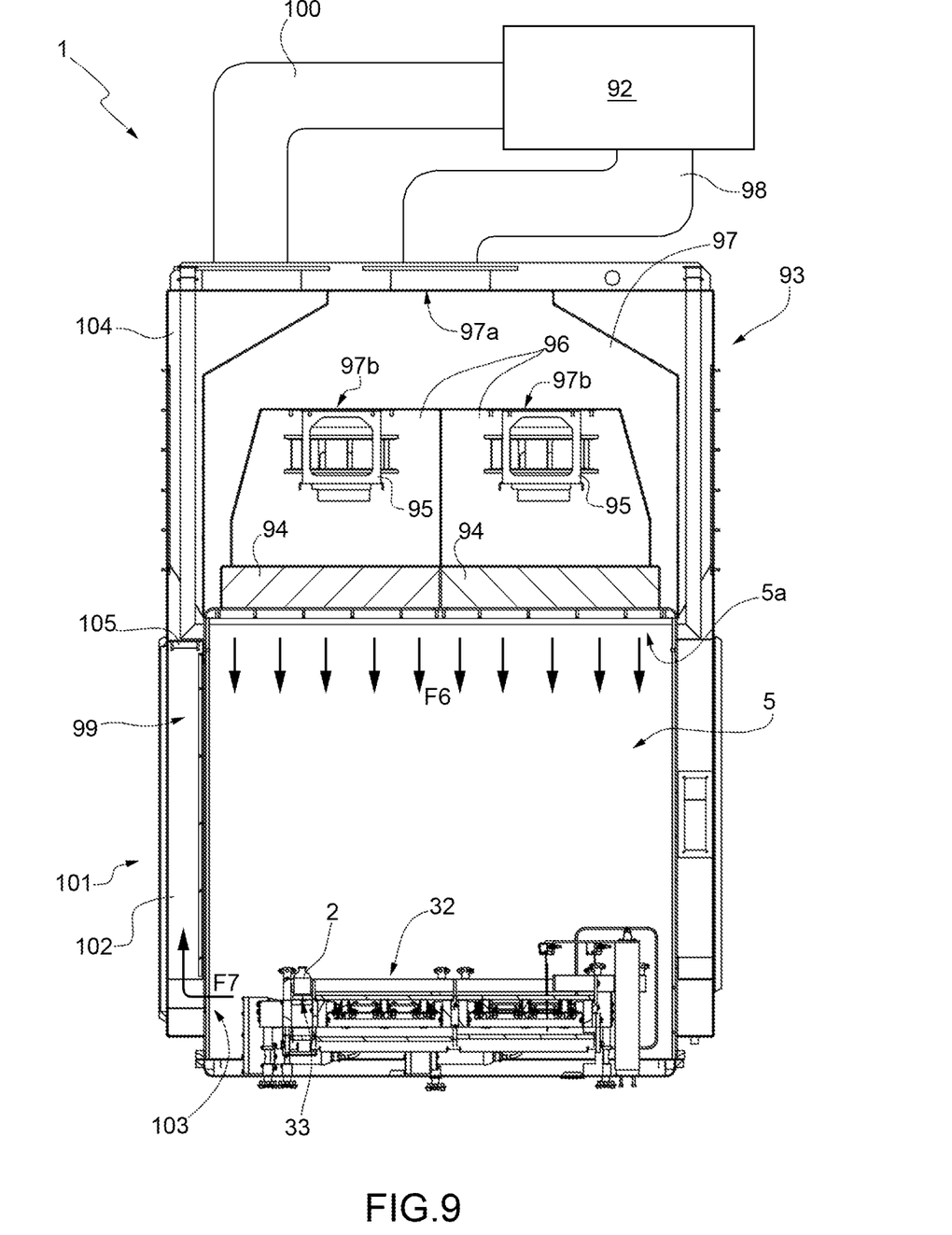
FIG. 9 illustrates an aeration chamber of the plant in FIGS. 1 and 2 according to a vertical cross-section view.

With reference to FIG. 9, the plant 1 comprises a dry air generator 92 and another forced ventilation system 93, which receives dry air from the dry air generator 92 and is connected to the aeration chamber 5 to generate therein a flow of dry air F6 oriented so as to hit the containers 2 present in the aeration chamber 5, arranged on the storage table 32, from above. In the following, "dry air" is defined as air having a relative humidity of less than 25%. Advantageously, the forced ventilation system 93 comprises a plurality of filters 94 arranged so as to define a ceiling 5*a* of the aeration chamber 5 and comprises at least one fan compressor 95 for pushing the dry air through the filters 94 so that the flow of dry air F6 is a laminar flow directed top-down.

In particular, the forced ventilation system 93 comprises one or more chambers 96 (FIG. 9 shows two chambers 96), each of which houses a corresponding fan compressor 95 and communicates with the aeration chamber 5 through a corresponding filter assembly 94, and an additional chamber 97, which partially surrounds the chambers 96 and comprises an inlet 97*a* connected to the dry air generator 92 through a delivery duct 98 and one or more outlets 97*b*, each of which is connected to, and in particular coincides with, the inlet of a corresponding fan compressor 95.

The aeration chamber 5 comprises a recirculation circuit 99, which connects the internal volume of the aeration chamber 5, at an area basically at the level of the storage table 32, to the dry air generator 92 through a return duct 100.

The recirculation circuit 99 is defined by one or more interconnecting cavities of an outer casing of the aeration chamber 5. In the example in FIG. 9, the outer casing of the aeration chamber 5 comprises a hatch 101 and the recirculation circuit 99 is partially defined in a cavity 102 of the hatch 101 that communicates with the inner volume of the aeration chamber 5 through a lower slot 103 formed on the inner face of the hatch 101 at the level of the storage table 32. A second cavity 104 of the recirculation circuit 99 is arranged above the hatch 101, wraps at least partially around the chamber 93, and communicates with the cavity 102 through an upper grid 105 of the hatch 101.

The electronic control unit of the plant 1 is configured to control the open-ring, dry air generator 92 to maintain the relative humidity of the dry air at a predetermined HRSET2 value of less than 25% and preferably ranging between 15% and 20%.

In use, the dry air arriving from the delivery duct 98 passes from the chamber 97 to the chambers 96 due to the suction action of the fan compressors 95. Inside each chamber 96, the corresponding fan compressor 95 pushes the air towards the corresponding filters 94 so as to generate, in the aeration chamber 5, the flow of dry air F6 that hits the containers 2 from above. The flow of dry air F6 touches the outer surface of the containers 2 removing from the surfaces and collecting the VHP residues. Air laden with VHP residues exits the aeration chamber 5 collected in a flow F7 that passes through the lower slot 103 of the hatch 101 to enter the recirculation circuit 99. The VHP-laden air exiting the aeration chamber 5 will undergo a catalysation process to remove the VHP.

The overall operation of the plant 1, controlled by the electronic control unit, is described below with reference to all the figures.

The shutter 47 is opened while the other shutter 48 is closed and the belt conveyor 12 receives the containers 2 one at a time through the inlet opening 7 so as to form one row of containers 2 in the compensation chamber 3, in front of the connection opening 8. When the row of containers 2 is formed, the shutter 47 is closed.

With the shutters 47 and 48 closed, the VHP generator 67 is commanded to feed the gaseous mixture of air and VHP to the delivery duct 91 in such an amount that in the compensation chamber 3, after a certain time interval ΔT3 predetermined by the closure of the shutter 47, a certain grade of particle contamination is reached, and in particular a grade A of particle contamination according to EEC-GMP standards.

At the end of the time interval ΔT3, the supply of the gaseous mixture to the delivery duct 91 is stopped, the shutter 48 is opened, the transfer system 13 transfers the row of containers 2 from the compensation chamber 3 to the decontamination chamber 4 through the connection opening 8, arranging it on the input side 22 of the tray 20, and the shutter 48 is closed again. The shutter 47 remains closed while the row of containers 2 is transferred.

At this point, before re-opening the shutter 47 to accommodate another row of containers 2, an air exchange is performed in the compensation chamber 3 to remove VHP residues.

The purpose of the compensation chamber 3 is, therefore, to allow the introduction of the containers 2 into the decontamination chamber 4 without there being any dispersion of VHP into the environment in which the plant 1 is located, and, at the same time, to keep the VHP concentration in the decontamination chamber 4 stable.

The VHP generator 67 is controlled to feed the gaseous mixture of air and VHP to the delivery ducts 73, 83, and 88 continuously and the forced ventilation system 68 is always active so that the flows of gaseous mixture F1 and F2 into the decontamination chamber 4 are continuous.

The shutters 48 and 66, connected to the connection openings 8 and 9, are normally held in the closed position if there is no row of containers 2 to enter or leave the decontamination chamber 4.

A suitable presence sensor (not illustrated) is arranged in the decontamination chamber 4 so as to detect when a row of containers 2 is present on the input side 22 of the tray 20 and, if present, the feeding system 25 is brought into the feeding configuration (FIG. 3) and then commanded to feed the pushing member 28 in the direction D3 so as to push the row of containers 2 that is on the input side 22 to a certain position of the tray 20, or against a previous row of containers 2 that is already present on the tray 20, so that the previous row of containers 2, in turn, is fed in the direction D3. The above sequence of operations is repeated each time a row of containers 2 enters the decontamination chamber 4. In this way, the decontamination chamber 4 is filled with a predetermined number of rows of containers 2.

An additional suitable presence sensor (not illustrated) is arranged in the decontamination chamber 4 so as to detect when a row of containers 2 is present on the output side 23 of the tray 20 and, if present, the feeding system 25 is brought into the unloading configuration (FIG. 4) and then commanded to feed the pushing member 29 in the direction D3 so as to push this row of containers 2 on the belt conveyor 26.

At this point, based on the signal provided by the presence sensor 65 (FIG. 6), the following operations are carried out. The shutter 66 is opened and the belt conveyor 26 is activated to feed the containers 2 towards the connection opening 9. When there are no more containers 2 on the belt conveyor 26 and the latter remain on the idle-roller plane 34, the belt conveyor 26 is stopped and the transfer system 35 pushes these containers 2 towards the connection opening 9. After that, the shutter 66 is closed.

The rate at which the containers 2 enter and leave the decontamination chamber is predetermined based on the number of rows of containers 2 that are on the tray 20 and a minimum time interval ΔT4 required for the microbiological load present on the containers 2 to be substantially reduced while the containers 2 are in the decontamination chamber 4.

The dry air generator 92 and the forced ventilation system 93 are always active so that the flow of dry air F6 into the aeration chamber 5 is continuous.

A suitable presence sensor (not illustrated) is arranged in the aeration chamber 5 so as to detect when the containers 2 enter through the connection opening 9 and, if present, the belt conveyor 33 and the storage table 32 are activated to convey to the storage table 32 and store therein the containers 2 that have just entered the aeration chamber 5. The storage table 32 is sized to hold a certain amount of containers 2 so that each container 2 remains in the aeration chamber 5 for a minimum time interval ΔT5 required for the flow of dry air F6 to remove any VHP residue from the surfaces of the containers 2.

Figures 10, 11:
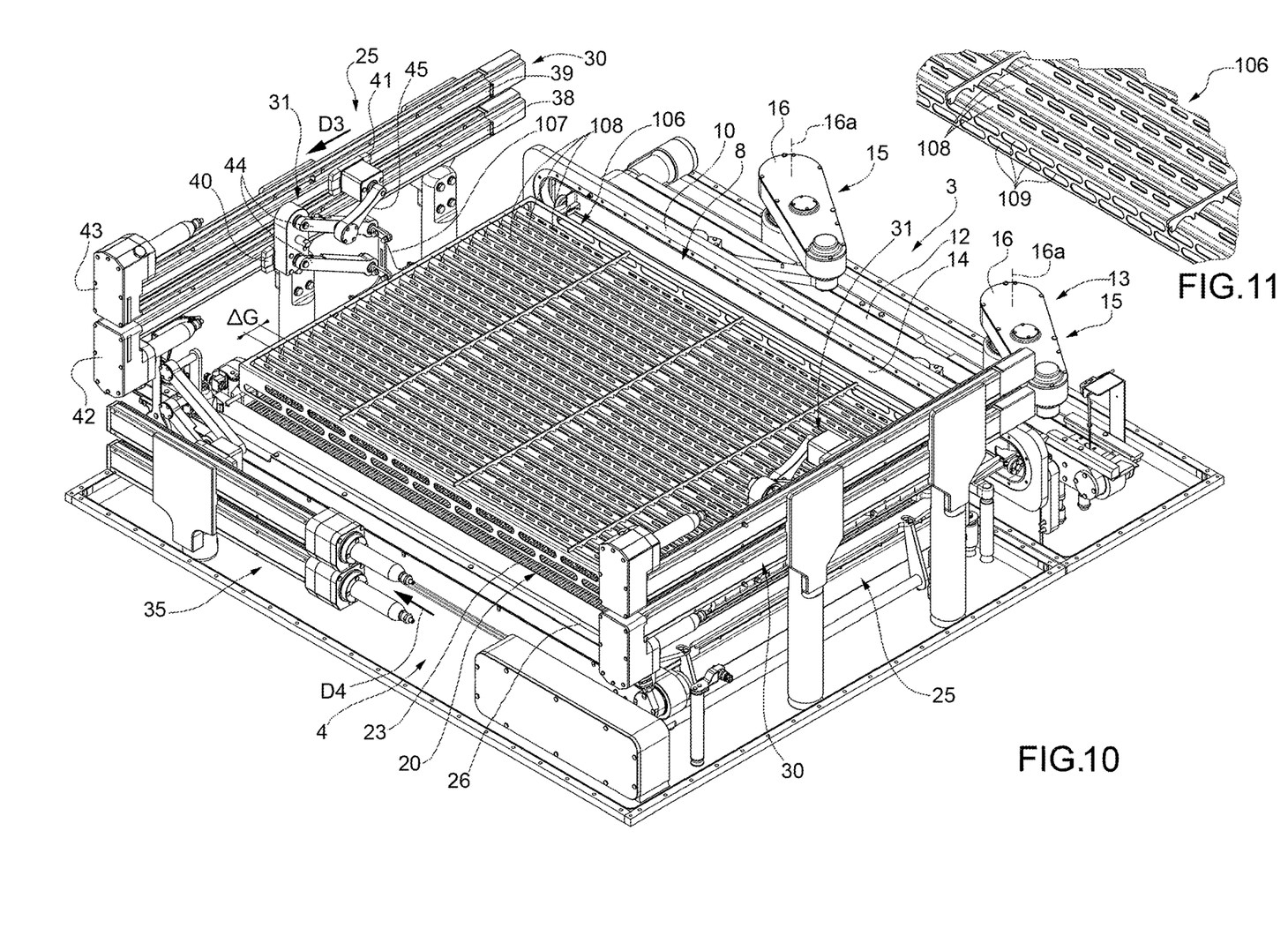
FIG. 10 illustrates, according to an axonometric view with some parts removed, an additional embodiment of the decontamination chamber of the plant in FIGS. 1 and 2.
FIG. 11 illustrates, in more detail, part of the embodiment in FIG. 10.

According to an additional embodiment illustrated in FIG. 10, the feeding system 25 differs from that illustrated in FIGS. 1-4 basically in that it comprises a feeding grid 106, instead of the pushing members 28 and 29. In particular, the two raising devices 31 support the feeding grid 106 from intermediate points of two respective sides thereof, basically parallel to the direction D3.

In addition, each raising device 31 of the embodiment illustrated in FIG. 10 differs from that illustrated in FIGS. 3-4 in that the slide 40 is further advanced than the slide 41 in the direction D3 and in that it does not have any arms 46 (FIGS. 3-4). The arms 44 connect the slide 40 to a respective side of the feeding grid 106 via a basically vertical bracket 107, again so as to make an articulated parallelogram.

The feeding grid 106 comprises a plurality of oblong elements 108, which extend transversely, and in particular orthogonally, to the direction D3, for a length at least equal to that of a row of containers 2 and are uniformly equidistant from each other along the direction D3 according to a distance ΔG so that the space between any pair of elements 108 adjacent to each other can receive a row of containers 2.

The feeding grid 106 basically extends across the area of the tray 20 in the direction D3 so that multiple rows of containers 2 can be simultaneously fed along the tray 20, each row being arranged between two adjacent elements 108, and transfer one row of containers 2 at a time from the output side 23 of the tray 20 to the belt conveyor 26. In other words, in use, each element 108 of the feeding grid 106, in use, acts as a pushing member to feed a corresponding row of containers 2. In addition, the penultimate element 108 of the feeding grid 106, in the order defined by the direction D3, acts as a pushing member to transfer the row of containers 2 from the output side 23 of the tray 20 to the belt conveyor 26.

Advantageously, the elements 108 of the feeding grid 106 are vertically oriented so as not to disturb the laminar pattern of the flow of gaseous mixture F1.

With reference to FIG. 11, advantageously the elements 108 present, for their whole extension, a plurality of openings 109 to reduce the contact points between the surface of the elements 108 and the surfaces of the containers 2 and, thus, reduce the risk of having small portions of surfaces that are not decontaminated because they are not touched by the gaseous mixture of air and VHP.

The electronic control unit of the plant 1 is configured to drive the electrical actuators 42 and 43 of each raising device 31 so as to move the feeding grid 106 up and down and back and forth in relation to the direction D3 in accordance with the so-called "reciprocating rolling", as described in greater detail below.

In a hypothetical initial position, the feeding grid 106 is raised above the maximum height of the containers 2 and moved towards the wall 10 of the connection opening 8. As soon as a row of containers 2 appears on the input side 22 of the tray 20, the feeding grid 106 is translated towards the wall 10 comprising the connection opening 8, i.e. in the opposite direction to the direction D3, and then lowered so that the row of containers 2 is arranged in the space between the first two elements 108 closest to the connection opening 8. The lowering of the feeding grid 106 is achieved by bringing the slides 40 and 41 to the minimum distance from each other.

At this point, the feeding grid 106 is translated in the direction D3 to feed the row of containers 2 according to a passage that has a width depending on the distance ΔG, then raised above the containers 2 and translated in the opposite direction to the direction D3 to be brought back to the initial position. The raising of the feeding grid 106 is achieved by bringing the slides 40 and 41 to the maximum distance from each other.

The cycle described above is repeated for each row of containers 2 entering the decontamination chamber 4 resulting in step-by-step feeding of the rows of containers 2 along the tray 20 until the same is filled.

When the tray 20 is full of containers 2, the first row of containers 2 that entered the decontamination chamber 4 will be on the output side 23 of the tray 20 and the subsequent translation step of the feeding grid 106 in the direction D3 will transfer this row of containers 2 to the conveyor 26.

The embodiment illustrated in FIGS. 10 and 11 has the advantage, compared to that illustrated in detail in FIGS. 3-4, of avoiding contact between adjacent rows of containers 2, thanks to the feeding grid 106 that keeps the rows of containers 2 separated from each other, and therefore of reducing the risk of having small portions of surfaces that are not decontaminated because they are not touched by the gaseous mixture of air and VHP. As mentioned above, the contact points between the surface of the elements 108 and the surfaces of the containers 2 are reduced due to the presence of the openings 109 along the elements 108.

According to an additional embodiment not illustrated, the dispenser system 82 comprises, instead of the dispenser bodies 84 illustrated in FIGS. 1 and 8, a single hollow body arranged below the tray and defining within it a chamber, which has a flat upper wall parallel to the tray 20 and having a plurality of through holes, uniformly distributed along this upper wall. The through holes in the body are then oriented from below towards the tray 20. In addition, this chamber is fed under pressure by the delivery duct 83 so that gaseous mixture exits the holes generating the turbulent-type flow of gaseous mixture F2 that hits the containers 2 from below.

According to another embodiment not illustrated, the slats 24 of the grid defining the tray 20 are not parallel to the direction D3, i.e. they are inclined in relation to the direction D3, so that the containers 2 of a certain row of containers 2 when they advance, because they are pushed by the pushing member 28 or by a subsequent row of containers 2, tend to rotate in relation to their longitudinal axis due to the rubbing of the bottom of the containers 2, which advance in the direction D3, on the slats 24, which are inclined in relation to the direction D3. In this way, the contact points between the side surfaces of the containers 2 change and, therefore, the possibility of having small portions of surfaces that are not decontaminated, since they are not touched by the gaseous mixture of air and VHP, is reduced.

According to an additional non-illustrated embodiment, the decontamination chamber 4 comprises, instead of the feeding system 25 and the tray 20, a belt conveyor, which is arranged to feed the row of containers 2 in the direction D2 and comprises a conveyor belt having a plurality of through-holes uniformly distributed along its surface. These through holes have the same function as the slots 21 of the tray 20.

According to an additional aspect of the invention, the plant 1 comprises control means, which are configured to control the vaporized hydrogen peroxide generating means 67 and the first forced ventilation means 68 so as to maintain the concentration of vaporized hydrogen peroxide in the decontamination chamber 4 at a predetermined VHPSET value ranging between 700 and 1200 ppm. The plant 1 preferably comprises a first sensor 89, which is arranged in the decontamination chamber 4 to measure the VHP concentration of vaporized hydrogen peroxide.

According to an additional aspect of the invention, the plant 1 comprises control means, which are configured to control the vaporized hydrogen peroxide generating means 67 and the first forced ventilation means 68 so as to maintain the relative humidity in the decontamination chamber 4 at a predetermined HRSET value ranging between 80% and 90%. The plant 1 preferably comprises a second sensor 90, which is arranged in the decontamination chamber 4 to measure the relative humidity.

The plant 1 described above in fact implements a method for continuously decontaminating containers 2, and, in particular, rigid containers, for example bottles, for containing pharmaceutical substances.

The main advantage of the plant 1 and the corresponding decontamination method described above is to make the decontamination process efficient and effective, thanks to the generation of two flows F1 and F2 of a gaseous mixture of air and VHP that hit the containers 2 to be decontaminated from above and below.

In addition, the decontamination can be repeated, due to the fact that the flows of gas mixture F1 and F2 are generated continuously and, therefore, can be controlled with extreme precision, and uniform, due to the fact that there is a laminar flow F1 from the side downwards and a turbulent flow F2 from the bottom up.

Finally, the decontamination process is relatively fast and can be integrated into a bottle filling and/or packaging line, thanks to the cascade connection of a compensation chamber 3, a decontamination chamber 4, and an aeration chamber 5, and to the presence of all motorised feeding and conveyance means within the above-mentioned chambers that move the containers 2 and transfer them from one chamber to the other.

The plant 1 and the method for decontaminating containers 2 are suitable for decontaminating any type of rigid container for pharmaceutical substances, for example bottles, tubs and nests.

The invention claimed is:

1. A plant to continuously decontaminate containers, the plant comprising:
    a decontamination chamber, which includes supporting means including a tray having a plurality of through openings and includes feeding means to feed at least one row of containers, which are aligned according to a first direction, along the tray in a second direction, which is transverse to the first direction;
    vaporized hydrogen peroxide generating means to generate a gaseous mixture including air and vaporized hydrogen peroxide;
    first forced ventilation means, which are connected to the vaporized hydrogen peroxide generating means to receive the gaseous mixture and to the decontamination chamber to generate, in the latter, a first flow of said gaseous mixture, which is oriented so as to hit the row of containers in the decontamination chamber from above; and
    dispenser means, which are connected to the vaporized hydrogen peroxide generating means to receive the gaseous mixture and are arranged under the tray to generate a second flow of said gaseous mixture, which is oriented so as to hit the row of containers in the decontamination chamber from below, through the through openings;
    wherein said feeding means include a feeding grid, which includes a plurality of pushing members defined by oblong elements extending transverse to the second direction and uniformly equidistant to each other along the second direction so that the space between any pair of pushing members adjacent to each other can accommodate a row of containers,
    wherein said tray has an input side and an output side for the row of containers;
    a compensation chamber, which includes an inlet designed to receive the containers and provided with a first hermetically sealing shutter, communicates with the decontamination chamber through a first connection opening provided with a second hermetically sealing shutter, and includes first conveyor means to receive the containers one at a time from the inlet and convey them according to said first direction so as to form one row of containers at a time in front of the first connection opening, and transfer means to transfer the row of containers from the compensation chamber to the decontamination chamber through the first connection opening up to the input side according to a third direction, which is transverse to the first direction.

2. The plant according to claim 1, wherein said first forced ventilation means include first filters, which are arranged so as to define a ceiling of the decontamination chamber, and first compressor means to push the gaseous mixture through the first filters so that said first flow of gaseous mixtures is a laminar flow; said pushing members are oriented vertically so as not to disturb the laminar flow.

3. The plant according to claim 1, wherein said dispenser means include at least one hollow body, which is designed to receive said gaseous mixture and has a plurality of through holes facing said tray so that said second flow of gaseous mixture is a turbulent flow.

4. The plant according to claim 1, wherein said feeding means include two guiding assemblies arranged on opposite sides of said tray, compared to a centerline of the tray parallel to said second direction, and two raising devices, which support said feeding grid on two corresponding sides and each of which is movably mounted along a corresponding guiding assembly to move the feeding grid parallel to the second direction.

5. The plant according to claim 4, wherein each of the two guiding assemblies includes two guides that are parallel to said second direction and each of the two raising devices includes two slides, each of which is slidably coupled to a corresponding guide via a corresponding recirculating ball screw driven by a corresponding electric actuator, an articulated parallelogram, which connects one side of the feeding grid to a first slide, and an arm, which connects, in an articulated way, the second slide to an intermediate point of the articulated parallelogram to enable an up-and-down movement of the feeding grid in correspondence with a reciprocal further apart and closer together movement of the two slides.

6. The plant according to claim 1, further comprising an aeration chamber, which communicates with the decontamination chamber through a second connection opening provided with a third hermetically sealing shutter; the decontamination chamber including second conveyor means arranged along the output side to convey the row of containers towards the second connection opening; said feeding means including at least one second pushing member to transfer a row of containers from the output side to said second conveyor means.

7. The plant according to claim 1, further comprising an aeration chamber, which communicates with the decontamination chamber through a second connection opening provided with a third hermetically sealing shutter; the decontamination chamber including second conveyor means arranged along the output side to convey the row of containers from the decontamination chamber to the aeration chamber through the second connection opening; the aeration chamber including conveying and storage means to receive the row of containers from the second connection opening and to store the containers inside the aeration chamber; the plant further comprising dry air generating means and second forced ventilation means, which are connected between the dry air generating means and the aeration chamber to generate, in the latter, a flow of dry air, which is oriented so as to hit the row of containers in the aeration chamber from above.

8. The plant according to claim 7, wherein said second forced ventilation means include second filters, which are arranged so as to define a ceiling of the aeration chamber, and second compressor means to push the dry air through the second filters so that said flow of dry air is a laminar flow.

9. A plant to continuously decontaminate containers, the plant comprising:
  a decontamination chamber, which includes supporting means including a tray having a plurality of through openings and includes feeding means to feed at least one row of containers, which are aligned according to a first direction, along the tray in a second direction, which is transverse to the first direction;
  vaporized hydrogen peroxide generating means to generate a gaseous mixture including air and vaporized hydrogen peroxide;
  first forced ventilation means, which are connected to the vaporized hydrogen peroxide generating means to receive the gaseous mixture and to the decontamination chamber to generate, in the latter, a first flow of said gaseous mixture, which is oriented so as to hit the row of containers in the decontamination chamber from above; and
  dispenser means, which are connected to the vaporized hydrogen peroxide generating means to receive the gaseous mixture and are arranged under the tray to generate a second flow of said gaseous mixture, which is oriented so as to hit the row of containers in the decontamination chamber from below, through the through openings;
  wherein said feeding means include a feeding grid, which includes a plurality of pushing members defined by oblong elements extending transverse to the second direction and uniformly equidistant to each other along the second direction so that the space between any pair of pushing members adjacent to each other can accommodate a row of containers,
  wherein said feeding means include two guiding assemblies arranged on opposite sides of said tray, compared to a centerline of the tray parallel to said second direction, and two raising devices, which support said feeding grid on two corresponding sides and each of which is movably mounted along a corresponding guiding assembly to move the feeding grid parallel to the second direction,
  wherein each of the two guiding assemblies includes two guides that are parallel to said second direction and each of the two raising devices includes two slides, each of which is slidably coupled to a corresponding guide via a corresponding recirculating ball screw driven by a corresponding electric actuator, an articulated parallelogram, which connects one side of the feeding grid to a first slide, and an arm, which connects, in an articulated way, the second slide to an intermediate point of the articulated parallelogram to enable an up-and-down movement of the feeding grid in correspondence with a reciprocal further apart and closer together movement of the two slides.

* * * * *